US009925377B2

(12) United States Patent
Moffitt et al.

(10) Patent No.: US 9,925,377 B2
(45) Date of Patent: Mar. 27, 2018

(54) SYSTEMS AND METHODS FOR PROVIDING THERAPY USING ELECTRICAL STIMULATION TO DISRUPT NEURONAL ACTIVITY

(71) Applicant: Boston Scientific Neuromodulation Corporation, Valencia, CA (US)

(72) Inventors: Michael A. Moffitt, Valencia, CA (US); Stephen Carcieri, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 6 days.

(21) Appl. No.: 14/861,415

(22) Filed: Sep. 22, 2015

(65) Prior Publication Data

US 2016/0082253 A1 Mar. 24, 2016

Related U.S. Application Data

(60) Provisional application No. 62/053,501, filed on Sep. 22, 2014.

(51) Int. Cl.
*A61N 1/00* (2006.01)
*A61N 1/36* (2006.01)

(52) U.S. Cl.
CPC ..... *A61N 1/36071* (2013.01); *A61N 1/36021* (2013.01); *A61N 1/36139* (2013.01); *A61N 1/36167* (2013.01); *A61N 1/36185* (2013.01)

(58) Field of Classification Search
CPC ........................ A61N 1/36071; A61N 1/36021
(Continued)

(56) References Cited

U.S. PATENT DOCUMENTS 4,813,418 A 3/1989 Harris
6,067,474 A 5/2000 Schulman et al.
(Continued)

FOREIGN PATENT DOCUMENTS

| DE | 10318071 A1 | 11/2004 |
| WO | 02/09808 A1 | 2/2002 |
| WO | 2009/055127 A1 | 4/2009 |

OTHER PUBLICATIONS

International Search Report and Written Opinion for PCT/US2015/051441 dated Mar. 3, 2016.
(Continued)

*Primary Examiner* — Nadia A Mahmood
(74) *Attorney, Agent, or Firm* — Lowe Graham Jones PLLC; Bruce E. Black

(57) ABSTRACT

A transcutaneous electrical-stimulation system includes a transcutaneous control module including a processor. The transcutaneous control module provides electrical-stimulation signals to electrode sets electrically-coupled to the transcutaneous control module. A first electrode set is electrically-coupled to the transcutaneous control module and is placed along patient skin over a first stimulation location. The first electrode set generates a first effective electric field suitable for transcutaneous stimulation of patient tissue at the first stimulation location. A second electrode set is electrically-coupled to the transcutaneous control module and is placed along patient skin over a second stimulation location. The second electrode set generates a second effective electric field suitable for stimulating patient tissue at the second stimulation location. The second effective electric field is time-delayed from the first effective electric field such that the second effective electric field is out of phase with the first effective electric field.

18 Claims, 11 Drawing Sheets

(58) Field of Classification Search
USPC .................................................... 607/2, 46
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,917,221 B2 | 3/2011 | Tass |
| 7,949,395 B2 | 5/2011 | Kuzma |
| 7,974,698 B2 | 7/2011 | Tass et al. |
| 7,974,706 B2 | 7/2011 | Moffitt et al. |
| 8,000,794 B2 | 8/2011 | Lozano |
| 8,000,795 B2 | 8/2011 | Lozano |
| 8,000,796 B2 | 8/2011 | Tass et al. |
| 8,078,275 B2 | 12/2011 | Lozano |
| 8,116,874 B2 | 2/2012 | Tass |
| 8,175,710 B2 | 5/2012 | He |
| 8,224,450 B2 | 7/2012 | Brase |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,346,365 B2 | 1/2013 | Lozano |
| 8,364,278 B2 | 1/2013 | Pianca et al. |
| 8,380,304 B2 | 2/2013 | Lozano |
| 8,391,985 B2 | 3/2013 | McDonald |
| 8,463,378 B2 | 6/2013 | Tass |
| 8,463,386 B2 | 6/2013 | Tass |
| 8,538,547 B2 | 9/2013 | Tass et al. |
| 8,565,883 B2 | 10/2013 | Lozano |
| 8,612,006 B2 | 12/2013 | Lozano et al. |
| 8,868,191 B2 | 10/2014 | Lozano |
| 9,227,066 B2 | 1/2016 | Lozano |
| 2003/0191506 A1 | 10/2003 | Shloznikov |
| 2004/0210271 A1 | 10/2004 | Campen |
| 2005/0075696 A1 | 4/2005 | Forsberg et al. |
| 2005/0216071 A1 | 9/2005 | Devlin et al. |
| 2006/0015153 A1 | 1/2006 | Bradford et al. |
| 2006/0212090 A1 | 9/2006 | Lozano et al. |
| 2007/0142874 A1 | 6/2007 | John |
| 2007/0150036 A1 | 6/2007 | Anderson |
| 2007/0225674 A1 | 9/2007 | Molnar et al. |
| 2008/0071325 A1 | 3/2008 | Bradley |
| 2008/0097530 A1* | 4/2008 | Muccio ............... A61N 1/0452 607/3 |
| 2008/0207985 A1* | 8/2008 | Farone ............... A61N 2/008 600/15 |
| 2008/0215113 A1 | 9/2008 | Pawlowicz |
| 2009/0082829 A1 | 3/2009 | Panken et al. |
| 2009/0112281 A1 | 4/2009 | Miyazawa et al. |
| 2009/0187222 A1 | 7/2009 | Barker |
| 2009/0276021 A1 | 11/2009 | Meadows et al. |
| 2010/0268298 A1 | 3/2010 | Pianca et al. |
| 2010/0076535 A1 | 5/2010 | Pianca et al. |
| 2011/0004267 A1 | 1/2011 | Meadows et al. |
| 2011/0077720 A1 | 3/2011 | Torgerson et al. |
| 2011/0078900 A1 | 4/2011 | Pianca et al. |
| 2011/0130817 A1 | 6/2011 | Chen |
| 2011/0130818 A1 | 6/2011 | Chen |
| 2011/0201977 A1 | 8/2011 | Tass |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0274273 A1 | 11/2012 | Jacobs et al. |
| 2012/0316615 A1 | 12/2012 | DiGiore et al. |
| 2013/0105071 A1 | 5/2013 | DiGiore et al. |
| 2013/0218239 A1 | 8/2013 | Grill et al. |
| 2013/0231713 A1 | 9/2013 | De Ridder |
| 2013/0289385 A1 | 10/2013 | Lozano et al. |
| 2013/0317583 A1 | 11/2013 | Pianca |
| 2013/0317585 A1 | 11/2013 | Barker |
| 2013/0317586 A1 | 11/2013 | Pianca |
| 2013/0317587 A1 | 11/2013 | Barker |
| 2013/0317588 A1 | 11/2013 | Howard et al. |
| 2014/0025133 A1 | 1/2014 | Lozano |
| 2014/0081349 A1 | 3/2014 | Lee et al. |
| 2014/0277281 A1 | 9/2014 | Grandhe |
| 2016/0030666 A1 | 2/2016 | Lozano et al. |

OTHER PUBLICATIONS

Larson, J. et al., "Reversal of LTP by theta frequency stimulation", Brain Research, Elsevier, Amsterdam, NL, vol. 600 No. 1, Jan. 8, 1993, pp. 97-102.

* cited by examiner

SYSTEMS AND METHODS FOR PROVIDING THERAPY USING ELECTRICAL STIMULATION TO DISRUPT NEURONAL ACTIVITY

CROSS-REFERENCE TO RELATED APPLICATIONS

This application claims the benefit under 35 U.S.C. § 119(e) of U.S. Provisional Patent Application Ser. No. 62/053,501, filed Sep. 22, 2014, which is incorporated herein by reference.

FIELD

The present invention is directed to the area of electrical stimulation systems and methods of using the systems. The present invention is also directed to systems and methods for providing therapy using electrical stimulation generated from electrical stimulation systems to disrupt undesired neural activity through desynchronization of action potential propagation along patient tissue using transcutaneous electrical nerve stimulation.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Implantable stimulation systems can include an implantable pulse generator (IPG), one or more leads, and an array of electrodes disposed along each lead. The electrodes are in contact with or near the nerves, muscles, or other tissue to be stimulated. The pulse generator generates electrical pulses that are delivered by the electrodes to body tissue.

Transcutaneous electrical nerve stimulation ("TENS") systems can be used to transcutaneously stimulate patient tissue using electrodes positioned along patient skin. TENS systems have been developed to provide non-invasive therapy to patients, including treatment of pain.

BRIEF SUMMARY

In one embodiment, a transcutaneous electrical stimulation system includes a transcutaneous control module having a processor. The transcutaneous control module is configured and arranged to provide electrical stimulation signals to multiple electrode sets electrically-coupled to the transcutaneous control module and is configured and arranged to remain external to a patient for transcutaneous electrical stimulation of patient tissue to treat patient pain. A first electrode set is electrically-coupled to the transcutaneous control module and is configured and arranged for placement along patient skin over a first stimulation location. The first electrode set is configured and arranged to communicate with the processor and to generate a first effective electric field suitable for transcutaneous stimulation of patient tissue at the first stimulation location using the electrical stimulation signals provided from the transcutaneous control module. A second electrode set is electrically-coupled to the transcutaneous control module and is configured and arranged for placement along patient skin over a second stimulation location. The second electrode set is configured and arranged to communicate with the processor and to generate a second effective electric field suitable for stimulating patient tissue at the second stimulation location using the electrical stimulation signals provided from the transcutaneous control module. The second effective electric field is time-delayed from the first effective electric field such that the second effective electric field is out of phase with the first effective electric field.

In some embodiments, the transcutaneous electrical stimulation system includes a sensor in communication with the processor, the sensor configured and arranged for monitoring patient theta band activity and detecting frequency shifts. In at least some embodiments, the transcutaneous control module is configured and arranged to provide the electrical stimulation signals to the first electrode set and the second electrode set in response to a first detected shift in frequency of the theta band activity. In at least some embodiments, the processor is configured and arranged for determining the time delay between the electrical stimulation signals within the first effective electric field and the electrical stimulation signals within the second effective electric field based on the first detected shift in frequency of the theta band activity. In at least some embodiments, the transcutaneous control module is configured and arranged to adjust at least one of amplitude, frequency, impedance, voltage, or pulse width of the electrical stimulation signals provided to the first electrode set and the second electrode set in response to a second detected shift in frequency of the theta band activity. In at least some embodiments, the transcutaneous control module is configured and arranged to terminate the electrical stimulation signals provided to the first electrode set and the second electrode set in response to a third detected shift in frequency of the theta band activity.

In at least some embodiments, the transcutaneous electrical stimulation system includes a processing unit in communication with the processor, the processing unit configured and arranged for coordinating with the processor to facilitate the positioning of the first electrode set and the second electrode set in the spinal cord of the patient.

In at least some embodiments, the transcutaneous electrical stimulation system includes a processing unit in communication with the processor, the processing unit configured and arranged for coordinating with the processor to adjust at least one of amplitude, frequency, impedance, voltage, or pulse width of at least one of the first effective electric field or the second effective electric field.

In at least some embodiments, the transcutaneous electrical stimulation system includes an actuator located external to the patient and in communication with the processor, the actuator configured and arranged for causing the transcutaneous control module to at least one of initiate providing the electrical stimulation signals to the at least one lead or terminate providing the electrical stimulation signals to the at least one lead.

In at least some embodiments, the transcutaneous electrical stimulation system includes a programming unit in communication with the processor, the programming unit configured and arranged for at least one of adjusting the time-delay between the first effective electric field and the second effective electric field, or select between two or more different electrode sets of the plurality of electrode sets for providing the transcutaneous electrical stimulation of patient tissue.

In another embodiment, a transcutaneous electrical stimulation system includes a transcutaneous control module including a processor. The transcutaneous control module is configured and arranged to provide electrical stimulation signals to multiple electrode sets electrically-coupled to the transcutaneous control module and is configured and arranged to remain external to a patient for transcutaneous electrical stimulation of patient tissue to treat patient pain. A first electrode set is electrically coupled to the transcutaneous control module and is configured and arranged for placement along patient skin. The first electrode set is configured and arranged to communicate with the processor and to generate a first effective electric field suitable for transcutaneously stimulating a first set of target neurons within patient tissue using the electrical stimulation signals provided from the transcutaneous control module. A second electrode set is electrically coupled to the transcutaneous control module and is configured and arranged for placement along patient skin. The second electrode set is configured and arranged to communicate with the processor and to generate a second effective electric field suitable for transcutaneously stimulating a second set of target neurons that is different from the first set of target neurons within patient tissue using the transcutaneous electrical stimulation signals provided from the transcutaneous control module. The second effective electric field has an overlap in volume of at least 50% with the first effective electric field.

In at least some embodiments, the second set of target neurons is a subset of the first set of target neurons. In at least some embodiments, the second set of target neurons is mutually exclusive of the first set of target neurons.

In yet another embodiment, an electrical stimulation system includes a transcutaneous control module having a first processor. The transcutaneous control module is configured and arranged to provide first electrical stimulation signals to a transcutaneous electrode set electrically-coupled to the transcutaneous control module for transcutaneous stimulation of patient tissue to treat patient pain. A transcutaneous electrode set is electrically-coupled to the transcutaneous control module and is configured and arranged for placement along patient skin. The transcutaneous electrode set is configured and arranged to communicate with the first processor and to generate a first effective electric field suitable for stimulating patient tissue at a first stimulation location using the first electrical stimulation signals provided from the transcutaneous control module. An implantable control module is configured and arranged for implantation in a body of the patient and has a second processor in communication with the first processor. The implantable control module is configured and arranged to provide second electrical stimulation signals to at least one implantable electrode electrically-coupled to the implantable control module for stimulation of patient tissue to treat patient pain. At least one implantable electrode is electrically-coupled to the implantable control module and is configured and arranged to communicate with the second processor and to generate a second effective electric field suitable for stimulating patient tissue at a second stimulation location using the second electrical stimulation signals provided from the implantable control module. The second effective electric field is coordinated with the first effective electric field.

In at least some embodiments, the second effective electric field is time-delayed from the first effective electric field such that the second effective electric field is out of phase with the first effective electric field.

In at least some embodiments, the electrical stimulation system includes a sensor in communication with at least one of the first processor or the second processor, the sensor configured and arranged for monitoring patient theta-band activity and detecting frequency shifts.

In at least some embodiments, the second effective electric field has an overlap in volume of no more than 20% with the first effective electric field.

In at least some embodiments, the first effective electric field is suitable for stimulating a first set of target neurons within patient tissue using the first electrical stimulation signals, wherein the second effective electric field is suitable for stimulating a second set of target neurons that is different from the first set of target neurons within patient tissue using the second electrical stimulation signals, and wherein the second effective electric field has an overlap in volume of at least 50% with the first effective electric field.

In at least some embodiments, the second set of target neurons is a subset of the first set of target neurons. In at least some embodiments, the second set of target neurons is mutually exclusive of the first set of target neurons.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of electrical stimulation systems and methods of using the systems. The present invention is also directed to systems and methods for providing therapy using electrical stimulation generated from electrical stimulation systems to disrupt undesired neural activity through desynchronization of action potential propagation along patient tissue using transcutaneous electrical nerve stimulation.

Transcutaneous electrical nerve stimulation ("TENS") systems use electrodes that are positioned along patient skin and that provide non-invasive therapy to patients, including treatment of pain. TENS systems include a pulse generator that generates electrical stimulation signals that are delivered transcutaneously to patient tissue via the electrodes. It may be advantageous to use TENS systems to treat patient pain due to the non-invasiveness of transcutaneous stimulation.

Figure 1A:
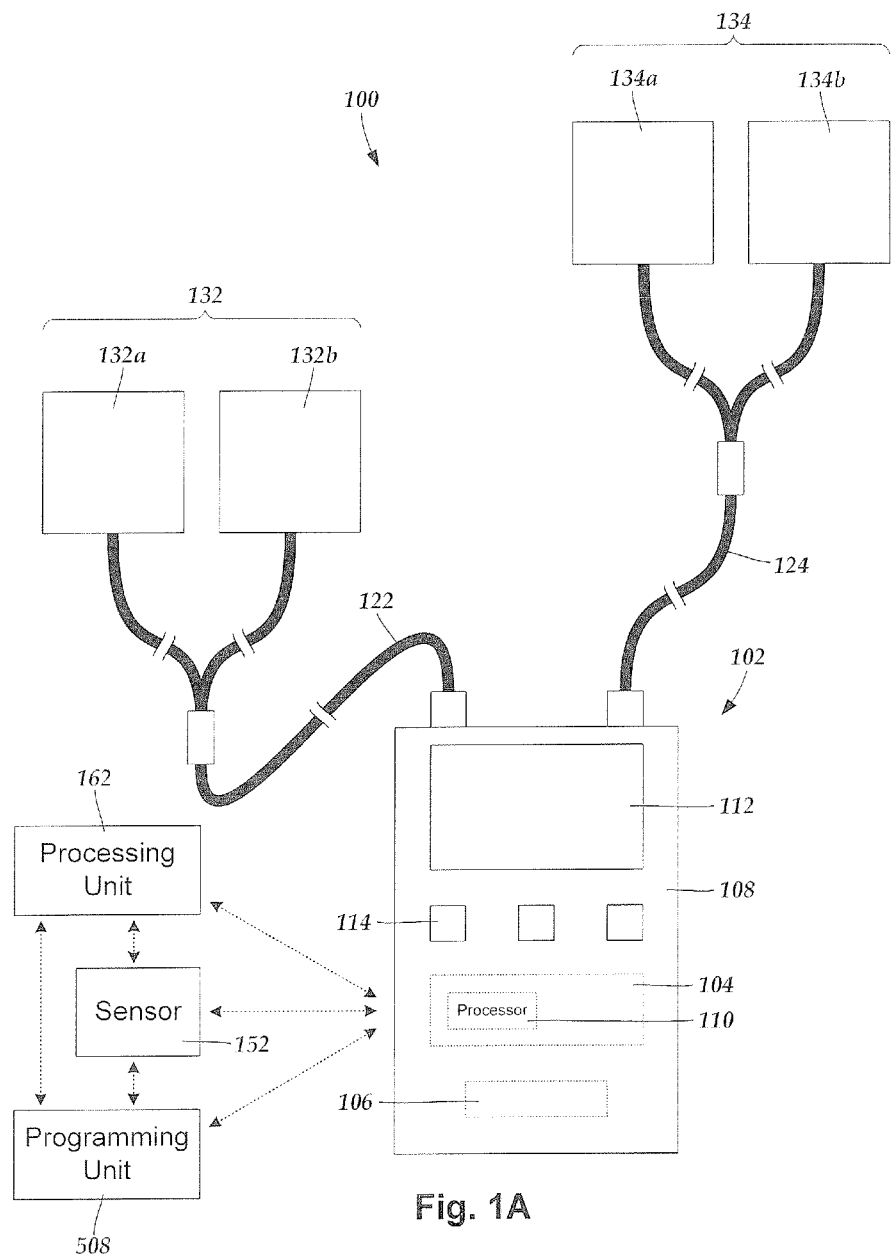
FIG. 1A is a schematic view of one embodiment of a transcutaneous electrical nerve stimulation system that includes transcutaneous electrodes electrically coupled to a transcutaneous control module, according to the invention.
Figure 1B:
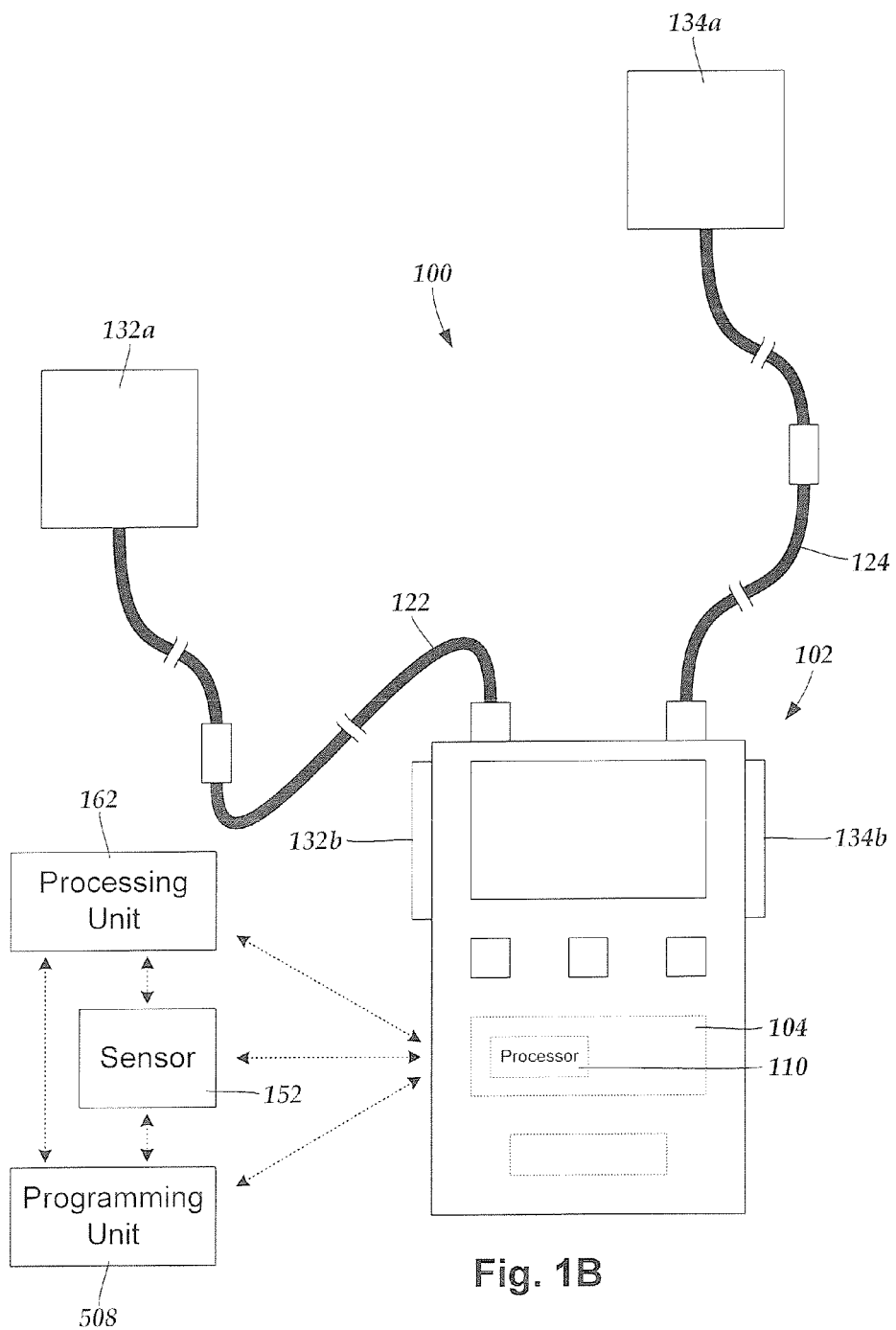
FIG. 1B is a schematic view of another embodiment of a transcutaneous electrical nerve stimulation system that includes transcutaneous electrodes electrically coupled to a transcutaneous control module, according to the invention.
Figure 1C:
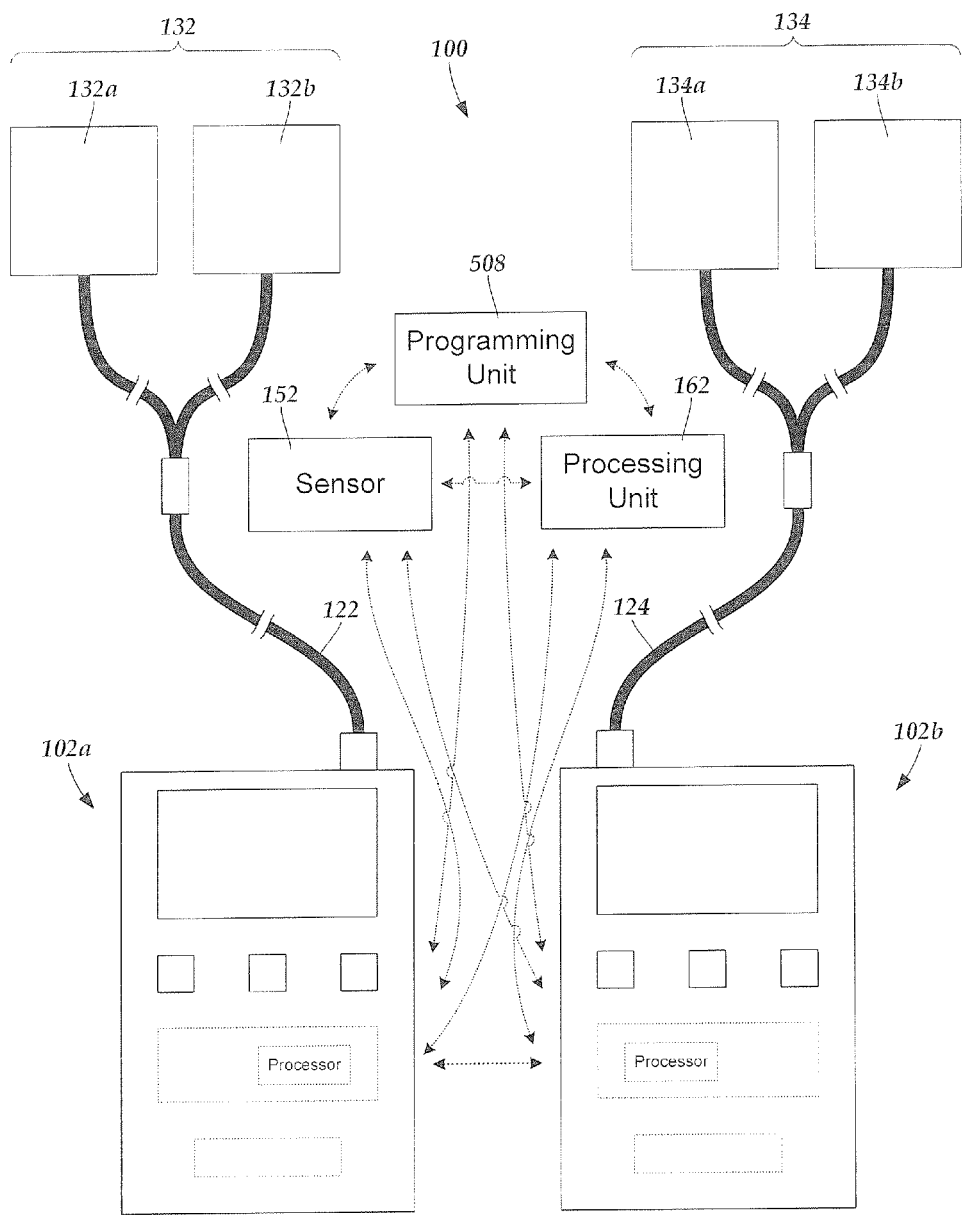
FIG. 1C is a schematic view of yet another embodiment of a transcutaneous electrical nerve stimulation system that includes transcutaneous electrodes electrically coupled to a transcutaneous control module, according to the invention.

FIGS. 1A-1C illustrate several different embodiments of a TENS system 100. In FIGS. 1A-1B, the TENS system 100 includes a single control module 102. In FIG. 1C, the TENS system 100 includes multiple control modules 102a and 102b. Any suitable number of control modules may be employed by the TENS system 100 (e.g., one, two, three, four, or more). Electrical stimulation leads 122 and 124 are coupleable to the one or more control modules. Any suitable number of electrical stimulation leads may be coupleable to the one or more control modules (e.g., one, two, three, four, or more).

An electronic subassembly 104 and an optional power source 106 are disposed in a housing 108 of the one or more control modules. A processor 110 is disposed in the electronic subassembly 104. The control module(s) may also include a display 112 and one or more operational controls 114.

An electrode set is disposed along each of the leads 122 and 124 and is electrically coupled to the electronic subassembly 104. The electrode sets can include any suitable number of electrodes (e.g., one, two, three, four, or more). In FIG. 1, electrode set 132 is disposed along the lead 122 and includes electrodes 132a and 132b. Similarly, FIG. 1 shows electrode set 134 disposed along the lead 124, and including electrodes 134a and 134b.

In at least some embodiments, the electrodes are formed as conductive pads designed for temporarily adhering to patient skin during a stimulation procedure. One or more of the electrodes 132a, 132b, 134a, 134b may include adhesive to promote position retention via temporary adherence to patient skin. One or more of the electrodes 132a, 132b, 134a, 134b may include a conductive gel to promote conduction of electrical stimulation signals between the electrodes and patient tissue.

During a stimulation procedure, the electrodes are disposed along patient skin over a target stimulation location. Electrical stimulation signals generated by the control module(s) propagate between two or more of the electrodes in a given electrode set such that at least some of the electrical stimulation signals pass through patient tissue along the target stimulation location. As shown in FIGS. 1A-1B, in at least some embodiments, multiple electrode sets are coupled to a single control module. As shown in FIG. 1B, in at least some embodiments, at least one electrode of an electrode set is disposed along the control module. As shown in FIG. 1C, the TENS system 100 may include multiple control modules. It will be understood that the TENS system 100 may include different combinations of the elements shown in FIGS. 1A-1C. For example, the TENS system 100 shown in FIG. 1C may include one or more electrodes of one or more of the electrode sets disposed along one or more of the control modules.

As herein described, an electrical stimulation system ("system") is used to deliver electrical stimulation signals to a target stimulation location at a site on or near a group of target neurons. The stimulation may, in some cases, reduce, or even eliminate patient pain.

In at least some embodiments, patient pain is reduced using two or more electrodes (or two or more sets of electrodes). As discussed below in more detail, electrical stimulation signals propagating through the two or more electrodes (or sets of electrodes) may be coordinated with time delays, or different stimulation parameters, or both. The two or more electrodes (or sets of electrodes) can either be in close physical proximity to one another, or physically spaced-apart from one another.

The two or more electrodes (or two or more sets of electrodes) may be disposed along a single lead or along multiple leads, or along the control module and a lead. When multiple leads are utilized, the multiple leads may be coupled to the same control module, or to separate control modules (see e.g., FIG. 1C) in communication with one another (to coordinate the stimulation timing and/or stimulation parameters).

The system includes transcutaneous stimulation provided via one or more transcutaneous leads. In at least some embodiments, the system is a combination system that includes stimulation provided via one or more implanted leads in addition to one or more transcutaneous leads. In which case, at least one of the two or more electrodes (or sets of electrodes) is configured and arranged to remain external to the patient during a stimulation procedure, while at least one other of the two or more electrodes (or sets of electrodes) is from an implanted system, such as implanted electrical stimulation system 200 (discussed below with reference to FIGS. 2-5), and is configured and arranged for being implanted in the patient during the stimulation procedure.

Figure 2:
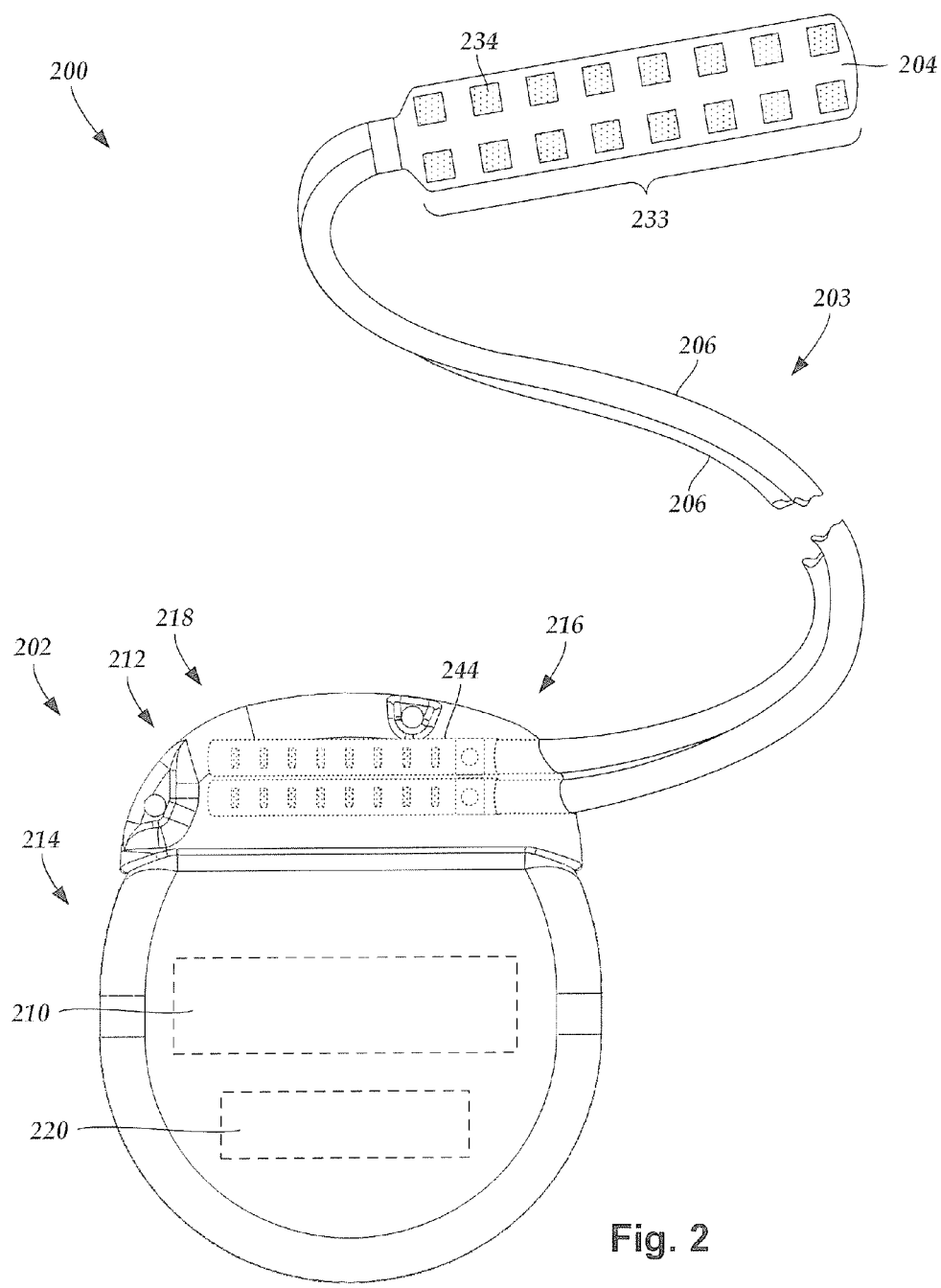
FIG. 2 is a schematic view of one embodiment of an implantable electrical stimulation system that includes a paddle lead electrically coupled to a control module, according to the invention.

Turning to FIG. 2, suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783, 359; 7,792,590; 7,809,446; 7,949,395; 7,974,706; 8,175, 710; 8,224,450; 8,271,094; 8,295,944; 8,364,278; and 8,391,985; U.S. Patent Applications Publication Nos. 2007/ 0150036; 2009/0187222; 2009/0276021; 2010/0076535; 2010/0268298; 2011/0004267; 2011/0078900; 2011/ 0130817; 2011/0130818; 2011/0238129; 2011/0313500; 2012/0016378; 2012/0046710; 2012/0071949; 2012/ 0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference.

FIG. 2 illustrates schematically one embodiment of an electrical stimulation system 200. The electrical stimulation system includes a control module (e.g., a device that includes a stimulator or pulse generator) 202 and a lead 203 coupleable to the control module 202. The lead 203 includes a paddle body 204 and one or more lead bodies 206. In FIG. 2, the lead 203 is shown having two lead bodies 206. It will be understood that the lead 203 can include any suitable number of lead bodies including, for example, one, two, three, four, five, six, seven, eight or more lead bodies 206. An array of electrodes 233, such as electrode 234, is disposed on the paddle body 204, and an array of terminals (e.g., 310 in FIG. 3A-3B) is disposed along each of the one or more lead bodies 206.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 3:
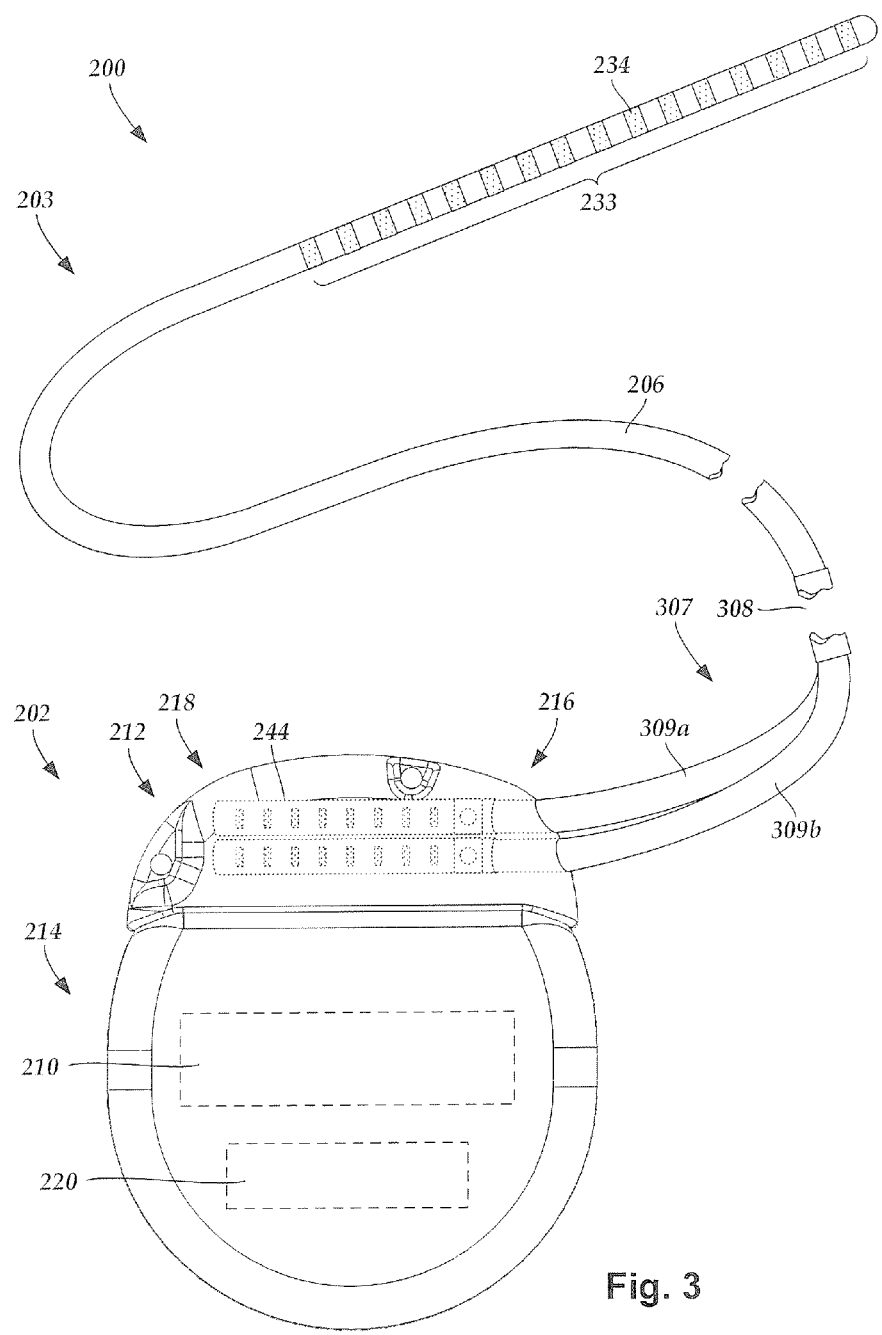
FIG. 3 is a schematic view of one embodiment of an implantable electrical stimulation system that includes a percutaneous lead electrically coupled to a control module, according to the invention.

FIG. 3 illustrates schematically another embodiment of the electrical stimulation system 200, where the lead 203 is a percutaneous lead. In FIG. 3, the electrodes 234 are shown disposed along the one or more lead bodies 206. In at least some embodiments, the lead 203 is isodiametric along a longitudinal length of the lead body 206.

Referring to both FIG. 2 and FIG. 3, the lead 203 can be coupled to the control module 202 in any suitable manner. In at least some embodiments, the lead 203 couples directly to the control module 202. In at least some other embodiments, the lead 203 couples to the control module 202 via one or more intermediate devices (400 in FIGS. 4A-4B). For example, in at least some embodiments one or more lead extensions 424 (see e.g., FIG. 4B) can be disposed between the lead 203 and the control module 202 to extend the distance between the lead 203 and the control module 202. Other intermediate devices may be used in addition to, or in lieu of, one or more lead extensions including, for example, a splitter, an adaptor, or the like or combinations thereof. It will be understood that, in the case where the electrical stimulation system 200 includes multiple elongated devices disposed between the lead 203 and the control module 202, the intermediate devices may be configured into any suitable arrangement.

In FIG. 3, the electrical stimulation system 200 is shown having a splitter 307 configured and arranged for facilitating coupling of the lead 203 to the control module 202. The splitter 307 includes a splitter connector 308 configured to couple to a proximal end of the lead 203, and one or more splitter tails 309a and 309h configured and arranged to couple to the control module 202 (or another splitter, a lead extension, an adaptor, or the like).

Referring to both FIG. 2 and FIG. 3, the control module 202 typically includes a connector housing 212, or "header", and a sealed electronics housing 214. An electronic subassembly 210 and an optional power source 220 are disposed in the sealed electronics housing 214. The connector housing 212 is disposed along a portion of an exterior surface of the sealed electronics housing 214 and includes a first end 216 and an opposing second end 218.

A control-module connector 244 is disposed in the connector housing 212. The control-module connector 244 is configured and arranged to receive, either directly or indirectly, a portion of the lead 203 and make an electrical connection between the lead 203 and the electronic subassembly 210 of the control module 202.

The electrical stimulation system, or components of the electrical stimulation system, including the paddle body 204, the one or more of the lead bodies 206, and the control module 202, are typically implanted into the body of a patient. The electrical stimulation system can be used for a variety of applications including, but not limited to deep brain stimulation, neural stimulation, spinal cord stimulation, muscle stimulation, and the like.

The electrodes 234 can be formed using any conductive, biocompatible material. Examples of suitable materials include metals, alloys, conductive polymers, conductive carbon, and the like, as well as combinations thereof. In at least some embodiments, one or more of the electrodes 234 are formed from one or more of: platinum, platinum iridium, or titanium.

Any suitable number of electrodes 234 can be disposed on the lead including, for example, one, two, three, four, five, six, seven, eight, nine, ten, eleven, twelve, fourteen, sixteen, twenty-four, thirty-two, or more electrodes 234. In the case of paddle leads, the electrodes 234 can be disposed on the paddle body 204 in any suitable arrangement. In FIG. 2, the electrodes 234 are arranged into two columns, where each column has eight electrodes 234.

The electrodes of the paddle body 204 (or one or more lead bodies 206) are typically disposed in, or separated by, a non-conductive, biocompatible material such as, for example, silicone, polyurethane, polyetheretherketone ("PEEK"), epoxy, and the like or combinations thereof. The one or more lead bodies 206 and, if applicable, the paddle body 204 may be formed in the desired shape by any process including, for example, molding (including injection molding), casting, and the like. The non-conductive material typically extends from the distal ends of the one or more lead bodies 206 to the proximal end of each of the one or more lead bodies 206.

In the case of paddle leads, the non-conductive material typically extends from the paddle body 204 to the proximal end of each of the one or more lead bodies 206. Additionally, the non-conductive, biocompatible material of the paddle body 204 and the one or more lead bodies 206 may be the same or different. Moreover, the paddle body 204 and the one or more lead bodies 206 may be a unitary structure or can be formed as two separate structures that are permanently or detachably coupled together.

Figure 4A:
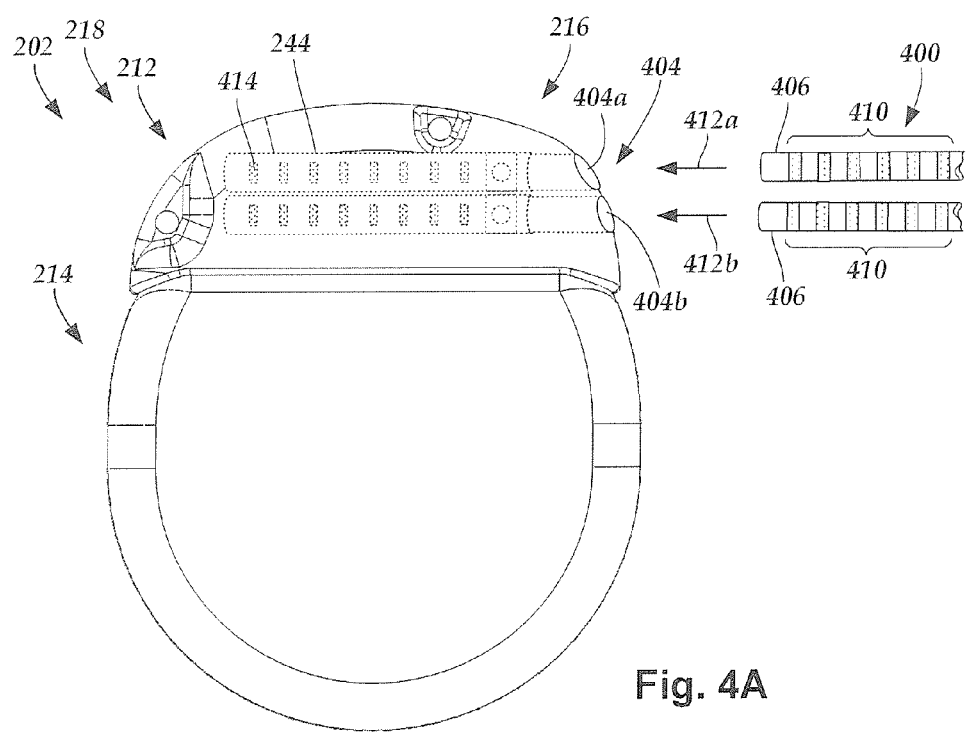
FIG. 4A is a schematic view of one embodiment of the control module of FIG. 2 and two elongated members of a lead assembly, the control module defining two lead-assembly ports configured for receiving the two elongated members of the lead assembly, the control module, according to the invention.
Figure 4B:
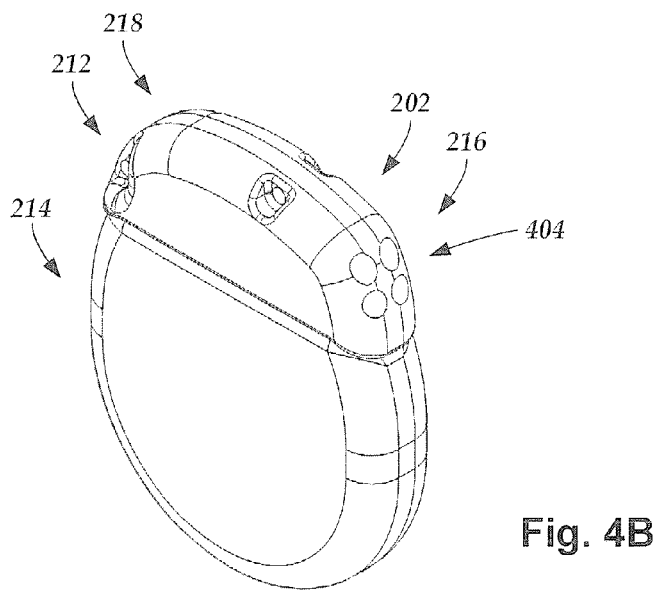
FIG. 4B is a schematic view of another embodiment of the control module of FIG. 2, the control module defining four lead-assembly ports configured for receiving up to four elongated members of one or more lead assemblies, the control module, according to the invention.

Terminals (e.g., 410 in FIGS. 4A-4B) are typically disposed along the proximal end portion of the one or more lead bodies 206 of the electrical stimulation system 200 (as well as along proximal end portions of any splitters, lead extensions, adaptors, or the like) for electrical connection to corresponding connector contacts (e.g., 414 in FIGS. 4A-4B). The connector contacts are disposed in connectors (e.g., 244 in FIGS. 2-4B; and 422 FIG. 4B) which, in turn, are disposed on, for example, the control module 202 (or along a distal end portion of a lead extension, a splitter, an adaptor, or the like). Electrically-conductive wires, cables, or the like ("conductors") (not shown) extend from, in the case of lead bodies, the terminals to the electrodes 234. In the case of intermediate devices (e.g., lead extensions, adaptors, splitters, or the like), the conductors extend from terminals to connector contacts of connectors (see e.g., connector contacts 440 of lead-extension connector 422 of FIG. 4C). Typically, one or more electrodes 234 are electrically coupled to each terminal. In at least some embodiments, each terminal is only connected to one electrode 234.

The conductors may be embedded in the non-conductive material of the lead body 206 (or other elongated members, such as lead extensions, splitters, adaptors, or the like) or can be disposed in one or more lumens (not shown) extending along the lead body 206 (or other elongated member). In some embodiments, there is an individual lumen for each conductor. In other embodiments, two or more conductors extend through a lumen. There may also be one or more stylet lumens (not shown) that open at, or near, the proximal end of the one or more lead bodies 206, for example, for inserting a stylet to facilitate placement of the one or more lead bodies 206 within a body of a patient. Additionally, there may be one or more lumens (not shown) that open at, or near, the distal end of the one or more lead bodies 206 (or other elongated members), for example, for infusion of drugs or medication into the site of implantation. In at least one embodiment, the one or more lumens are flushed continually, or on a regular basis, with saline, epidural fluid, or the like. In at least some embodiments, the one or more lumens are permanently or removably sealable along distal ends of the lumens.

FIG. 4A is a schematic side view of one embodiment of proximal end portions of two elongated members 406 of a lead assembly 400 configured and arranged for coupling to one embodiment of the control-module connector 244. The elongated members 406 of the lead assembly 400 may include, for example, one or more of the lead bodies (e.g., the lead bodies 206 of FIG. 2 or FIG. 3), one or more intermediate devices (e.g., the splitter 307, the lead extension 424 of FIG. 4C, an adaptor, or the like or combinations thereof), or a combination thereof.

The control-module connector 244 defines at least one lead-assembly port 404 into which a proximal end portion of the lead assembly 400 can be inserted, as shown by directional arrows 412a and 412b. In FIG. 4A (and in other figures), the connector housing 212 is shown having two lead-assembly ports 404a and 404b. The connector housing 212 can define any suitable number of lead-assembly ports including, for example, one, two, three, four, five, six, seven, eight, or more lead-assembly ports. FIG. 4B illustrates an alternate embodiment of the control module 202 with four lead-assembly ports 404 disposed in the connector housing 212. The lead-assembly ports 404 shown in each of FIGS. 4A-4B extend from the first end 216 of the connector housing 212.

As shown in FIG. 4A, the control-module connector 244 also includes a plurality of connector contacts, such as connector contact 414, disposed within each lead-assembly port 404a and 404b. When the one or more lead assemblies 400 are inserted into the one or more lead-assembly ports 404a and 404b, the connector contacts 414 can be aligned with terminals 410 disposed along the proximal end portion(s) of the one or more lead assemblies 400 to electrically couple the control module 202 to the electrodes (234 of FIG. 2 or 3). Examples of connectors in control modules are found in, for example, U.S. Pat. Nos. 7,244,150 and 8,224,450, which are incorporated by reference.

Figure 4C:
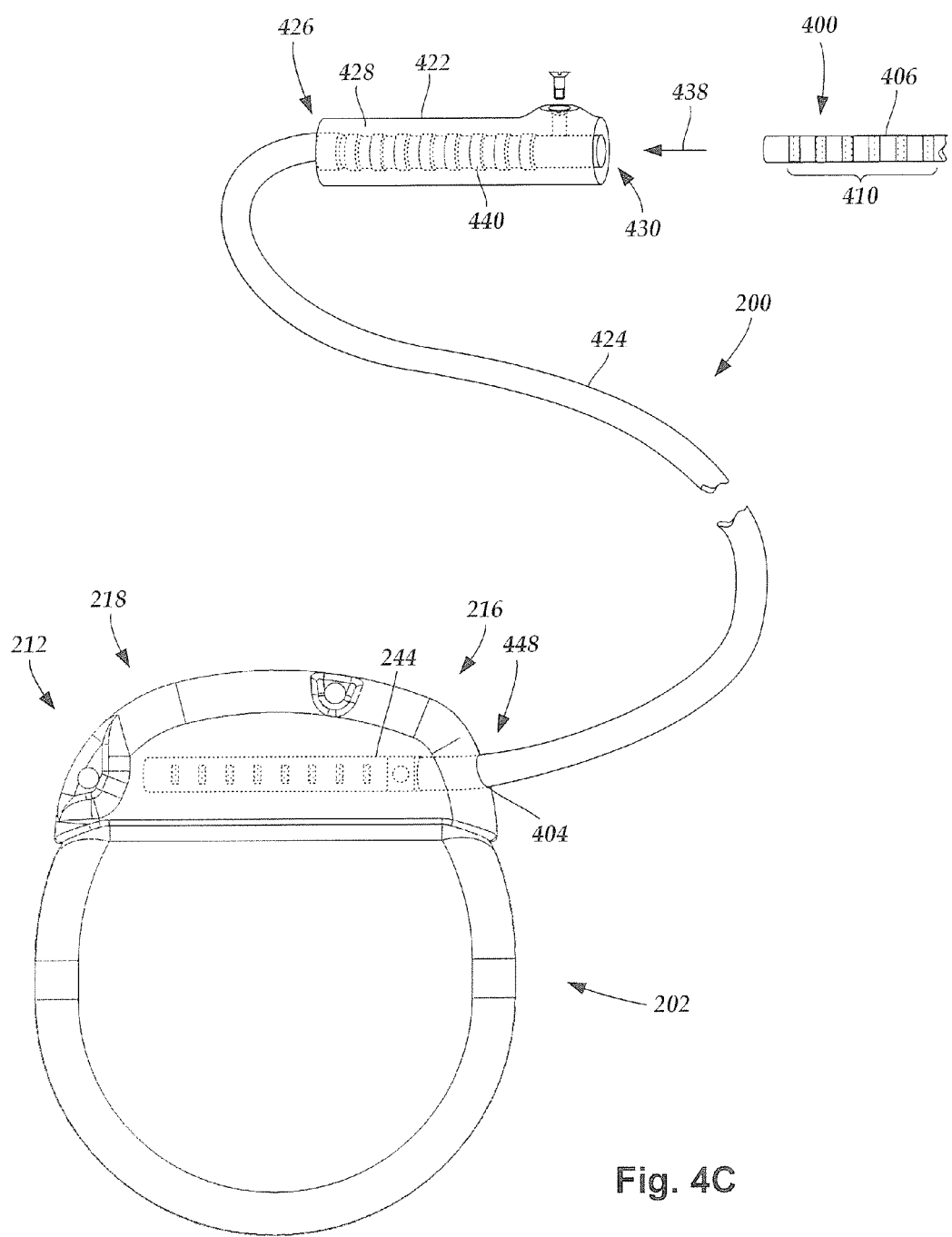
FIG. 4C is a schematic view of one embodiment of an elongated member of the lead assembly of FIG. 4A and a lead extension coupled to the control module of FIG. 2, the lead extension configured to receive the elongated member, according to the invention.

FIG. 4C is a schematic side view of another embodiment of the electrical stimulation system 200. The electrical stimulation system 200 includes a lead extension 424 that is configured and arranged to couple one or more elongated members (e.g., one or more lead bodies, splitters, adaptors, another lead extension, or the like or combinations thereof) of the lead assembly 400 to the control module 202. In FIG. 4B, the lead extension 424 is shown coupled to a single lead-assembly port 404 defined in the control-module connector 244. Additionally, the lead extension 424 is shown configured and arranged to couple to a single elongated member 406. In alternate embodiments, the lead extension 424 is configured and arranged to couple to multiple lead-assembly ports 404 defined in the control-module connector 244, or to receive multiple elongated members, or both.

A lead-extension connector 422 is disposed on the lead extension 424. In FIG. 4B, the lead-extension connector 422 is shown disposed along a distal end portion 426 of the lead extension 424. The lead-extension connector 422 includes a connector housing 428. The connector housing 428 defines at least one lead-assembly port 430 into which terminals 410 of the elongated device can be inserted, as shown by directional arrow 438. The connector housing 428 also includes a plurality of connector contacts, such as connector contact 440. When the elongated device 406 is inserted into the lead-assembly port 430, the connector contacts 440 disposed in the connector housing 428 can be aligned with the terminals 410 of the elongated device to electrically couple the lead extension 424 to the electrodes (234 of FIGS. 2 and 3) disposed along the lead (203 in FIGS. 2 and 3).

In at least some embodiments, a proximal end portion 448 of the lead extension 424 is similarly configured and arranged as a proximal end portion of the lead 203 (or other elongated member 406). The lead extension 424 may include a plurality of conductors (not shown) that electrically couple the connector contacts 440 to the proximal end portion 448 of the lead extension 424 that is opposite to the distal end portion 426. In at least some embodiments, the conductors disposed in the lead extension 424 can be electrically coupled to a plurality of terminals (not shown) disposed along the proximal end portion 448 of the lead extension 424. In at least some embodiments, the proximal end portion 448 of the lead extension 424 is configured and arranged for insertion into a connector disposed in another lead extension (or another intermediate device). In other embodiments (and as shown in FIG. 4B), the proximal end portion 448 of the lead extension 424 is configured and arranged for insertion into the control-module connector 244.

Figure 5:
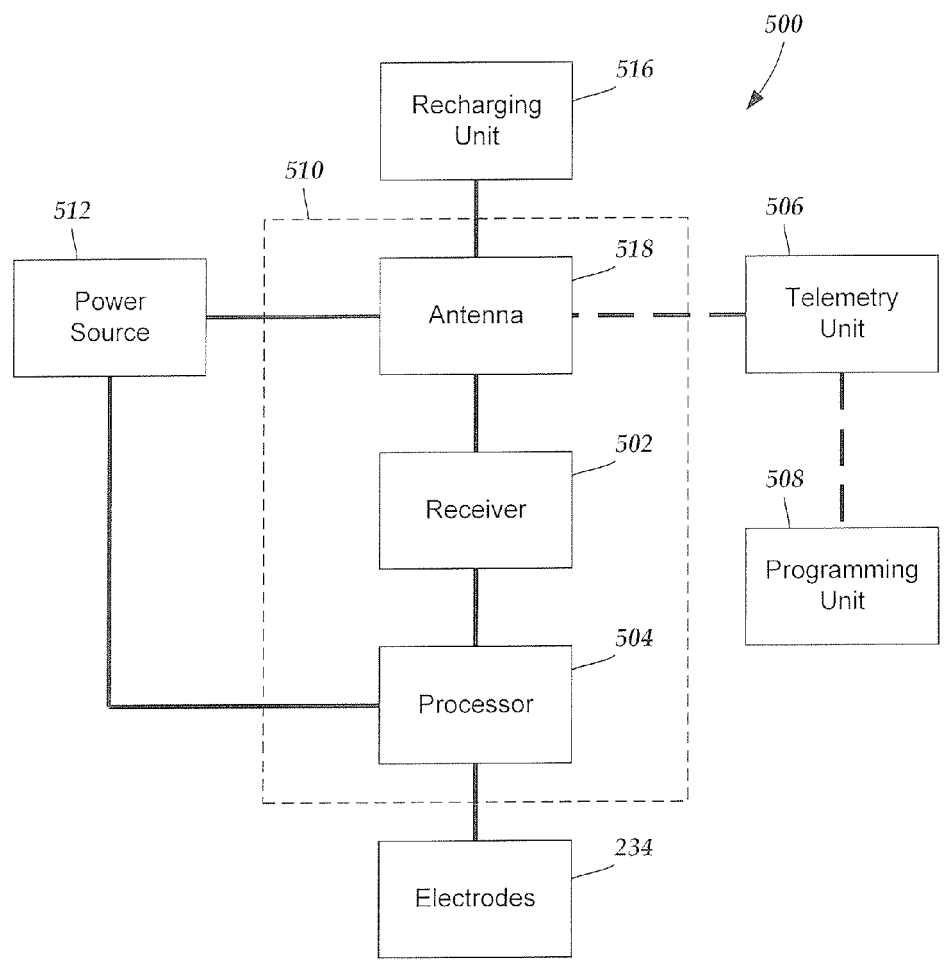
FIG. 5 is schematic overview of one embodiment of components of a stimulation system, including an electronic subassembly disposed within a control module, according to the invention.

FIG. 5 is a schematic overview of one embodiment of components of an electrical stimulation system 500 including an electronic subassembly 510 disposed within a control module. It will be understood that the electrical stimulation system can include more, fewer, or different components and can have a variety of different configurations including those configurations disclosed in the stimulator references cited herein. It will also be understood that the control module (102 in FIG. 1) may include the same, or similar, components to the components shown in, and described with reference to, FIG. 5.

Some of the components (for example, a power source 512, an antenna 518, a receiver 502 and a processor 504) of the electrical stimulation system can be positioned on one or more circuit boards or similar carriers within a sealed housing of an implantable pulse generator, if desired. Any power source 512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 518 or a secondary antenna. The external power source can be in a device that is mounted on the skin of the user or in a unit that is provided near the user on a permanent or periodic basis.

If the power source 512 is a rechargeable battery, the battery may be recharged using the optional antenna 518, if desired. Power can be provided to the battery for recharging by inductively coupling the battery through the antenna to a recharging unit 516 external to the user. Examples of such arrangements can be found in the references identified above.

In one embodiment, electrical stimulation signals (e.g., electrical current) is emitted by the electrodes 234 on the paddle or lead body to stimulate nerve fibers, muscle fibers, or other body tissues near the electrical stimulation system. The processor 504 is generally included to control the timing and electrical characteristics of the electrical stimulation system. For example, the processor 504 can, if desired, control one or more of the timing, frequency, strength, duration, and waveform of the pulses. In addition, the processor 504 can select which electrodes can be used to provide stimulation, if desired. In some embodiments, the processor 504 selects which electrode(s) are cathodes and which electrode(s) are anodes. In some embodiments, the processor 504 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 508 that, for example, allows modification of pulse characteristics. In the illustrated embodiment, the processor 504 is coupled to a receiver 502 which, in turn, is coupled to the optional antenna 518. This allows the processor 504 to receive instructions from an external source to, for example, direct the pulse characteristics and the selection of electrodes, if desired.

In one embodiment, the antenna 518 is capable of receiving signals (e.g., RF signals) from an external telemetry unit 506 which is programmed by the programming unit 508. The programming unit 508 can be external to, or part of, the telemetry unit 506. The telemetry unit 506 can be a device that is worn on the skin of the user or can be carried by the user and can have a form similar to a pager, cellular phone, or remote control, if desired. As another alternative, the telemetry unit 506 may not be worn or carried by the user but may only be available at a home station or at a clinician's office. The programming unit 508 can be any unit that can provide information to the telemetry unit 506 for transmission to the electrical stimulation system 500. The programming unit 508 can be part of the telemetry unit 506 or can provide signals or information to the telemetry unit 506 via a wireless or wired connection. One example of a suitable programming unit is a computer operated by the user or clinician to send signals to the telemetry unit 506.

The signals sent to the processor 504 via the antenna 518 and the receiver 502 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 500 to cease operation, to start operation, to start charging the battery, or to stop charging the battery. In other embodiments, the stimulation system does not include the antenna 518 or receiver 502 and the processor 504 operates as programmed.

Optionally, the electrical stimulation system 500 may include a transmitter (not shown) coupled to the processor 504 and the antenna 518 for transmitting signals back to the telemetry unit 506 or another unit capable of receiving the signals. For example, the electrical stimulation system 500 may transmit signals indicating whether the electrical stimulation system 500 is operating properly or not or indicating when the battery needs to be charged or the level of charge remaining in the battery. The processor 504 may also be capable of transmitting information about the pulse characteristics so that a user or clinician can determine or verify the characteristics.

As mentioned above, electrical stimulation systems ("systems") can be used to deliver electrical stimulation signals to target stimulation locations at sites on or near groups of target neurons. The stimulation may, in some cases, reduce, or even eliminate patient pain using two or more electrodes (or two or more sets of electrodes) coordinated with time delays, or different stimulation parameters, or both. The two or more electrodes (or sets of electrodes) can either be in close physical proximity to one another, or physically spaced-apart from one another. The two or more electrodes (or two or more sets of electrodes) may be disposed along a single lead or along multiple leads.

The system includes stimulation provided using one or more transcutaneous leads of the TENS system (see e.g., 100 in FIGS. 1A-1C). In at least some embodiments, the system is a combination system that also includes stimulation provided using one or more implanted leads of the implanted stimulation system (see e.g., 200 in FIGS. 2-5) in addition to stimulation provided using one or more transcutaneous leads of the TENS system. In which case, at least one of the two or more electrodes (or sets of electrodes) delivers stimulation to the patient from a location external to the patient, and at least one of the two or more electrodes (or sets of electrodes) delivers stimulation to the patient from a location internal to the patient.

It will be understood that when the system includes both transcutaneous leads and implanted leads, multiple processors may be used. In at least some embodiments, when multiple processors are used, such as the processors 110 and 504, the processors are in communication with one another to coordinate actions, such as providing stimulation, adjusting stimulation parameters (e.g., amplitude, frequency, impedance, voltage, pulse width, or the like), terminating stimulation, and the like.

In at least some embodiments, the two or more electrodes (or sets of electrodes) are positioned in proximity to the patient's spinal cord. When the two or more electrodes (or sets of electrodes) are positioned in proximity to the patient's spinal cord, the two or more electrodes (or sets of electrodes) may be positioned along the same spinal cord level, or different spinal cord levels. The implanted electrode (s) may be implanted in the patient's epidural space, or in proximity to one or more dorsal root ganglia, dorsal horn, dorsal column, or some combination thereof. Examples of electrical stimulation systems suitable for stimulating dorsal root ganglia are found in, for example, U.S. Patent Applications Publication Nos. 2013/0317583; 2013/0317585;

2013/0317586; 2013/0317587; and 2013/0317588, all of which are incorporated by reference.

Electrical stimulation (using the TENS system, the implantable system, or a combination of both) typically involves delivering electrical stimulation signals to one or more target stimulation locations at a site on or near a group of target neurons. The size, intensity, and character of the stimulation may be controlled by adjusting the stimulation parameters (e.g., amplitude, frequency, impedance, voltage, pulse width, or the like) of the electrical stimulation signals. The stimulation may, in some cases, reduce, or even eliminate patient pain.

Patient pain may be identified by any suitable technique including, for example, using a pain measurement scale, patient feedback, a change in one or more monitored pain indicators, or the like. One pain indicator that may be identifiable and observable is a frequency shift in the patient's theta wave activity. It has been shown that frequency shifts in a patient's theta wave activity (e.g., approximately 4 Hz to 8 Hz) may indicate the presence of patient pain. Observed shifts in the frequencies of theta wave activity have been shown to correlate to an undesired neuronal activity (e.g., propagation of action potentials along one or more neural pathways). While not wishing to be held to any particular theory, electrical stimulation may provide therapy to a patient by disrupting undesired neural activity through desynchronization of action potential propagation along patient tissue.

Frequency shifts may include, for example, a shift of at least 0.2 Hz, 0.5 Hz, 0.8 Hz, 1 Hz, 2 Hz, 3 Hz, 4 Hz, 5 Hz, or more. Frequency shifts may include a shift to a particular frequency or frequency range. Frequency shifts may include a change in a pattern of the theta-wave activity. The frequency shifts may be observed using any sensor suitable recording of electrical activity, such as via electroencephalography, or other similar technique. The measured activity can be measured against a known (e.g., previously-recorded) patient base line reading, or compared to a known population, or both.

In at least some embodiments, the patient (or medical practitioner) may be able to initiate stimulation, as needed, using the TENS system (by itself or in combination with the implantable stimulation system). For example, the patient (or medical practitioner) may be able to initiate stimulation in response to patient pain by using an actuator (e.g., a switch) that is external to the patient and that is in communication with the one or more control modules.

The stimulation may last for a set period of time (e.g., a minute, an hour a day, a week, or longer). Alternatively, the stimulation may last until it is manually terminated (e.g., by the patient or the medical practitioner). As discussed below, the stimulation may also be terminated automatically in response to feedback.

Turning briefly back to FIGS. 1A-1C, in some embodiments one or more pain indicators are monitored. For example, in some embodiments, neural activity within the patient's theta-wave band is monitored (e.g., via one or more sensors in communication with the one or more control modules). In which case, the electrical stimulation (by itself or in combination with the implantable stimulation system) may be intermittently performed in response to an observed pain indicator, such as a frequency shift in the theta band. In at least some embodiments, the system includes a sensor 152 that is in communication with the one or more control modules and that senses a pain indicator, such as frequency shifts in the theta band and signals initiation of electrical stimulation in response to the observed frequency shift.

In some embodiments, the system employs feedback to adjust one or more stimulation parameters (e.g., amplitude, frequency, impedance, voltage, pulse width, or the like) after a period of stimulation. For example, stimulation may be adjusted based on an observed change in theta wave activity towards or away from a particular undesired observed frequency or frequency range, or towards or away from a particular desired frequency or frequency range.

In some embodiments, the system employs feedback to terminate stimulation. Termination of stimulation may be in response to changes in the patient's theta wave band after a period of stimulation. For example, stimulation may be terminated upon a return to the patient's base line theta wave activity, or in response to a move away from a particular undesired observed frequency or frequency range.

In at least some embodiments, the neuronal activity desired to be disrupted is synchronous. In some embodiments, the electrical stimulation signals generated by the two or more electrodes (or sets of electrodes) create effective electric fields (e.g., electrical stimulation propagating from the electrodes sufficient to cause an excitatory effect on axons surrounding the electrodes) that function to reset the undesired neural activity in a coordinated manner.

In order to generate sufficient effective electric fields for disrupting the undesired neuronal activity, the two or more electrodes (or sets of electrodes) may employ the same stimulation parameters, or may have one or more different stimulation parameters. The size and shape of the effective electric fields generated by the two or more electrodes (or sets of electrodes) at a given set of stimulation parameters can be determined by observation of the effects of stimulation. Alternately (or additionally), the size and shape of the effective electric fields generated by the two or more electrodes (or sets of electrodes) at a given set of stimulation parameters can be determined, or stimulated, using one or more computer models (e.g., Volume of Tissue Activated Model, Stimulation Field Model, or the like or combinations thereof).

As indicated above, the effective volume of an electric field is based on the region of tissue that experiences a stimulating effect in response to the electric field. Outside this effective volume, the electric field is too weak to stimulate the tissue. Information obtained from the computer models may facilitate selection of implantation locations, or facilitate selection of stimulation parameters, or both. The computer models may be implemented through the one or more processors (110 in FIGS. 1A-1C and 504 in FIG. 5), or may be incorporated into a processing unit 162 in communication with the one or more processors. The processing unit 162 can be disposed in one of the control modules, or may be a stand-alone unit.

In some embodiments, the two or more electrodes (or sets of electrodes) generate effective electric fields that are temporally offset (e.g., time-delayed) from one another such that the effective electric fields are out of phase from one another. In at least some embodiments, the two or more electrodes (or sets of electrodes) are situated such the effective electric fields generated by the two or more electrodes (Or sets of electrodes) stimulate different populations of neurons in communication with one another (e.g., different neurons along a particular neural pathway). Although not wishing to be bound by a particular theory, the offsetting of the effective electric fields generated by the two or more electrodes (or sets of electrodes) may be such that the downstream neurons are in a refractory period while the upstream neurons are propagating action potentials. In which case, the action potentials may be unable to propagate from the upstream neurons to the downstream neurons. Accordingly, undesired neuronal activity may be desynchronized and, therefore, disrupted.

Any suitable time delay may be implemented between the two or more electrodes (or sets of electrodes) for disrupting undesired neuronal activity. In some embodiments, the time delay may be determined by testing and observation. In some embodiments, the time delay is determined based on the frequency of the undesired neural activity (e.g., an observed shifted theta-band frequency) to be desynchronized. For example, in at least some embodiments N electrodes, where N is the number of different electrodes (or sets of electrodes) (or populations of neurons to be desynchronized) greater than or equal to 2, are driven such that there is a time delay of $1/(f \times N)$, where f is a frequency that is on or around the frequency of the undesired neural activity (e.g., an observed shifted theta-band frequency) to be desynchronized. In some embodiments, f is the same as the frequency as the undesired neuronal activity. In other embodiments, f is within 10 Hz, 9 Hz, 8 Hz, 7 Hz, 6 Hz, 5 Hz, 4 Hz, 3 Hz, 2 Hz, or 1 Hz above or below the frequency of the undesired neuronal activity.

Optionally, the programming unit 508 may be utilized to control and adjust stimulation (e.g., the time-delay between stimulation signals from the two or more electrodes (or sets of electrodes), select between different electrodes (or sets of electrodes) for providing stimulation. The programming unit 508 may additionally enable the user (or medical practitioner, or both) to control other stimulation features (e.g., one or more stimulation parameters, the period of time of stimulation, termination of stimulation, and the like or combinations thereof). The programming unit 508 may, optionally, be in communication with one or more of the sensor 152, the processing unit 162, or both. The sensor 152 and processing unit 162 may also be in communication with one another.

When the generated effective electric fields are time-delayed from one another, it may be desirable for the effective electric fields to have little or no overlap in order to coordinate the resetting of the action potential propagation by stimulating different populations of cells that are in communication with one another. In at least some embodiments, the two or more electrodes (or sets of electrodes) are situated such that the nearest outer edges of the generated effective electric fields are at least 1 cm, 2 cm, 3 cm, 4 cm, or 5 cm apart from one another. In at least some embodiments, the two or more electrodes (or sets of electrodes) are situated such that the nearest outer edges of the generated effective electric fields are no more than 5 cm, 4 cm, 3 cm, 2 cm, or 1 cm apart from one another. In at least some embodiments, the two or more electrodes (or sets of electrodes) are situated such that there is little (no more than 20%, 10%, 5%, or less), if an overlap in the effective volumes of the generated effective electric fields.

Alternately, the two or more electrodes (or sets of electrodes) are situated such that the effective electric fields generated by the two or more electrodes (or sets of electrodes) have substantial (at least 50%, 60%, 70%, 80%, 90%, 95%, or more of the effective volumes of the electric fields) overlap. When there is substantial overlap of effective electric fields between the two or more electrodes (or sets of electrodes), the stimulation parameters of the two or more electrodes (or sets of electrodes) may be varied from one another in order to preferentially target some neurons more than others.

It has been shown that some stimulation parameters may preferentially target some neurons more than others. At least some physical characteristics of neurons (e.g., axon diameters, the presence or absence of a myelin sheath, or the like) may affect whether or not those neurons are excited by an effective electric field having a particular set of stimulation parameters. Consequently, in at least some embodiments, the stimulation parameters of at least one of the generated effective electric fields is varied in response to one or more physical characteristics of the neurons along the overlapping portion of the generated effective electric fields (e.g., axon diameters, the presence or absence of a myelin sheath, or the like).

The different stimulation parameters may enable a first set of stimulation parameters of a first electrode (or set of first electrodes) to stimulate a first set of target neurons and a second set of stimulation parameters of a second electrode (or set of second electrodes) to stimulate a second set of target neurons. The first electrode (or set of first electrodes) can be disposed on either an implanted lead or a transcutaneous lead. Similarly, the second electrode (or set of second electrodes) can be disposed on either an implanted lead or a transcutaneous lead.

In some embodiments, the second set of target neurons is a subset of the first set of target neurons. In which case, one example of a stimulation procedure may include only a portion of the overall population of neurons within an overlapping portion of the effective electric fields becoming excitable during stimulation by a first electrode (or set of electrodes) with a first set of stimulation parameters, while all (or nearly all) of the overall population of neurons within the overlapping portion of the effective electric fields becoming excitable during stimulation by a second electrode (or set of electrodes) with a second set of stimulation parameters.

In other embodiments, the second set of target neurons is mutually exclusive of the first set of target neurons. In which case, one example of a stimulation procedure may include a first portion of the overall population of neurons within an overlapping portion of the effective electric fields becoming excitable during stimulation by a first electrode (or set of electrodes) with a first set of stimulation parameters, and a second portion (mutually exclusive of the first portion) of the overall population of neurons within the overlapping portion of the effective electric fields becoming excitable during stimulation by a second electrode (or set of electrodes) with a second set of stimulation parameters.

In at least some embodiments, stimulation can be timed between the two or more electrodes (or sets of electrodes) such that some neurons are in a refractory period while other neurons are propagating action potentials. In which case, at least some of the action potentials are unable to propagate along the entire length of the neuronal pathway. Accordingly, undesired neuronal activity may be disrupted through desynchronization.

Figure 6:
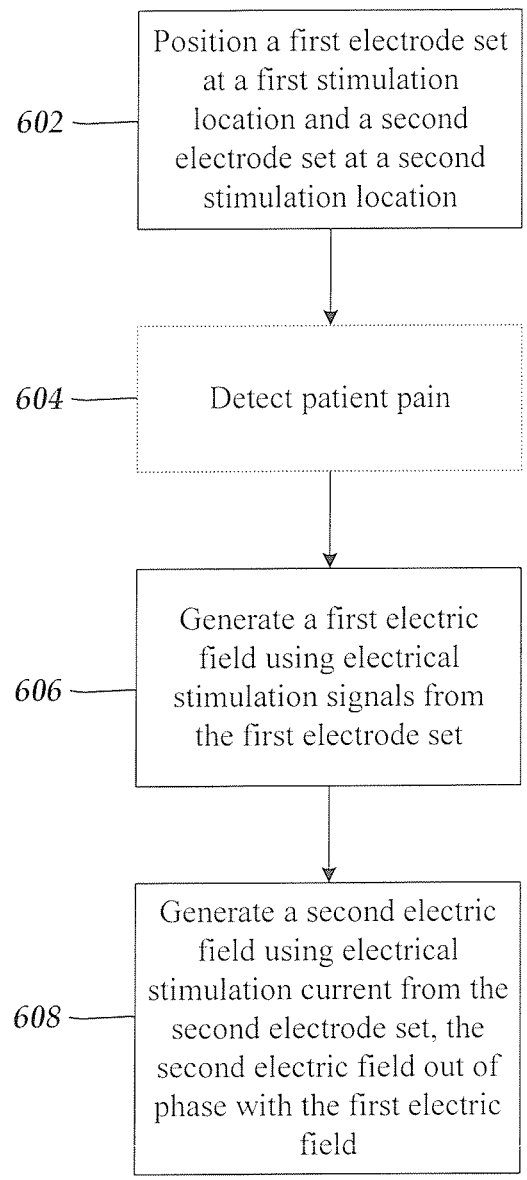
FIG. 6 is a flowchart of one embodiment of a technique for disrupting undesired neural activity through desynchronization of action potential propagation along patient tissue, according to the invention.
Figure 7:
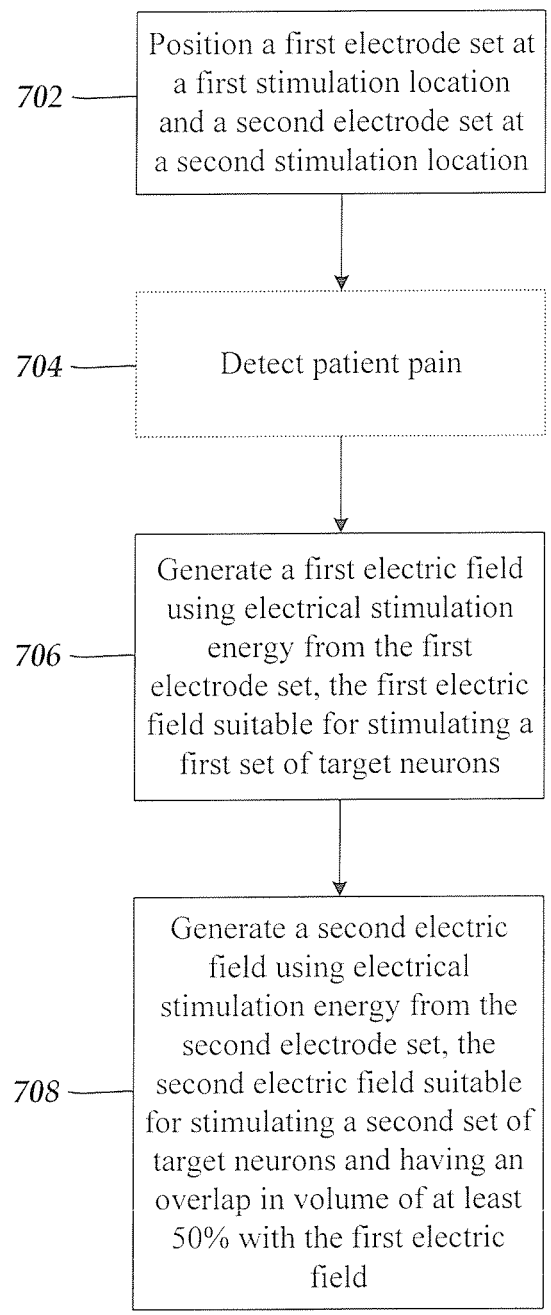
FIG. 7 is a flowchart of another embodiment of a technique for disrupting undesired neural activity through desynchronization of action potential propagation along patient tissue, according to the invention.
Figure 8:
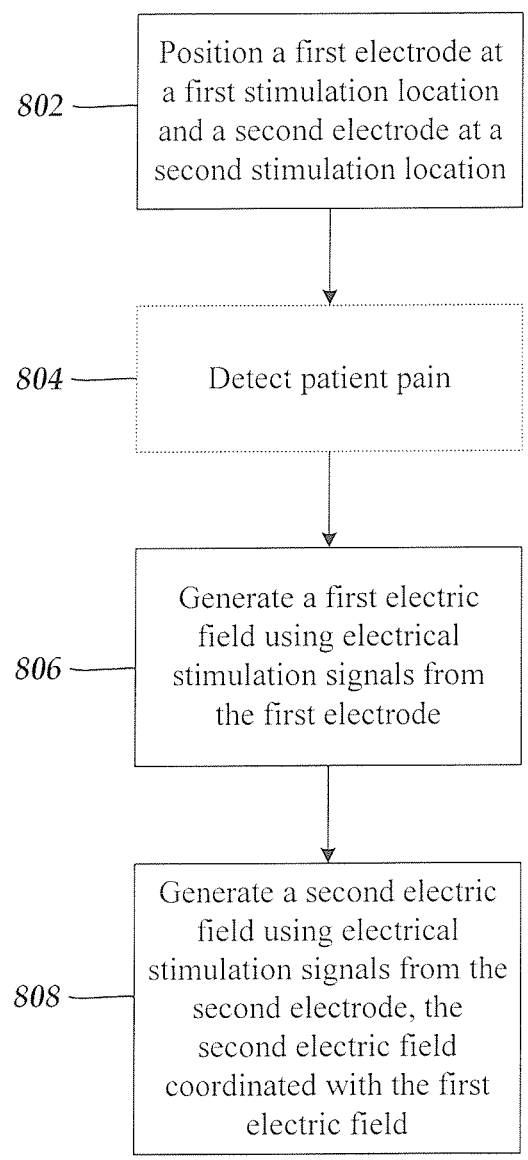
FIG. 8 is a flowchart of yet another embodiment of a technique for disrupting undesired neural activity through desynchronization of action potential propagation along patient tissue, according to the invention.

FIGS. 6-8 are flowcharts showing several different techniques for stimulating patient tissue to alleviate patient pain. FIG. 6 is a flowchart showing one embodiment of a stimulation procedure for disrupting undesired neural activity through desynchronization of action potential propagation along patient tissue. In step 602, first and second electrode sets are positioned at first and second stimulation locations, respectively. The first electrode set and the second electrode set are configured and arranged for providing transcutaneous stimulation. Positioning the first and second electrode sets at first and second stimulation locations, respectively, may, optionally, include removably adhering the electrodes to the patient's skin. A computer model may be used to facilitate the determination of the positioning of the electrodes.

Optionally, in step 604, patient pain is detected. The pain may be detected using an suitable technique including, for example, a pain measurement scale, patient feedback, a change in one or more monitored pain indicators (e.g., a frequency shift in the patient's theta wave activity), or the like. The pain indicator, such as a frequency shift, can be detected using any suitable monitoring technique (e.g., electroencephalography, or the like). The monitoring of the pain indicator can be performed using a sensor in communication with the control module.

In step 606, a first effective electric field is generated using electrical stimulation energy from the first electrode set. In step 608, a second effective electric field is generated using electrical stimulation energy from the second electrode set, with the second effective electric field being time-delayed (e.g., out of phase) from the first effective electric field. The time-delay between the first and second effective electric fields may, optionally, be calculated based on a frequency of a detected undesired neural activity.

The generated second effective electric field may be either non-overlapping or partially (e.g., no more than 20%) overlapping with the first effective electric field. The second effective electric field can have stimulation parameters that are either the same or different from stimulation parameters of the first effective electric field. A computer model may be used to adjust the stimulation parameters of first and second effective electric fields generated by the first and second electrode sets, respectively. The computer model(s) can be used to adjust the location, the size, the shape (or any combination of the above) so that the generated effective electric fields are non-overlapping, or partially overlapping. Stimulation, via the first and second electrode sets, may be initiated in response to the pain indicator, such as the detected frequency shift in the patient's theta band activity. The frequencies of the first and second effective electric fields can be based, at least in part, on the pain indicator, such as the frequency of the detected shift in theta band activity. The stimulation parameters of the first and/or second effective electric fields may be adjusted in response to a feedback loop, such as an observed frequency shift towards or away from a particular frequency or frequency range. The stimulation may be terminated in response to a feedback loop, such as an observed frequency shift towards or away from a particular frequency or frequency range.

FIG. 7 is a flow diagram showing another embodiment of a stimulation procedure for disrupting undesired neural activity through desynchronization of action potential propagation along patient tissue. In step 702, first and second electrode sets are positioned at first and second stimulation locations, respectively. The first electrode set and the second electrode set are configured and arranged for providing transcutaneous stimulation. Positioning the first and second electrode sets at first and second stimulation locations, respectively, may, optionally, include removably adhering the electrodes to the patient's skin. A computer model may be used to facilitate the determination of the positioning of the electrodes.

Optionally, in step 704, patient pain is detected. The pain may be detected using any suitable technique including, for example, a pain measurement scale, patient feedback, a change in one or more monitored pain indicators (e.g., a frequency shift in the patient's theta wave activity), or the like. The pain indicator, such as a frequency shift, can be detected using any suitable monitoring technique (e.g., electroencephalography, or the like). The monitoring of the pain indicator can be performed using a sensor in communication with the control module.

In step 706, a first effective electric field is generated using electrical stimulation signals from the first electrode set. The first effective electric field is suitable for stimulating a first set of target neurons. In step 708, a second effective electric field is generated using electrical stimulation signals from the second electrode set. The second effective electric field is suitable for stimulating a second set of target neurons. The second effective electric field has on overlap in volume of at least 50% with the first effective electric field. The second set of target neurons can be a subset of the first set of target neurons, or mutually exclusive of the first set of target neurons. The stimulation parameters of the first and second effective electric fields may be calculated based on one or more physical characteristics of at least some of the neurons in the overlapping portion of the first and second effective electric fields. The one or more physical characteristics may include, for example, axon diameters, the presence or absence of a myelin sheath, or the like.

A computer model may be used to adjust the stimulation parameters of first and second effective electric fields generated by the first and second electrode sets, respectively. The computer model(s) can be used to adjust the location, the size, the shape (or any combination of the above) so that the generated effective electric fields are substantially overlapping. Stimulation, via the first and second electrode sets, may be initiated in response to the pain indicator, such as the detected frequency shift in the patient's theta band activity. The frequencies of the first and second effective electric fields can be based, at least in part, on the pain indicator, such as the frequency of the detected shift in theta band activity. The stimulation parameters of the first and/or second effective electric fields may be adjusted in response to a feedback loop, such as an observed frequency shift towards or away from a particular frequency or frequency range. The stimulation may be terminated in response to a feedback loop, such as an observed frequency shift towards or away from a particular frequency or frequency range.

FIG. 8 is a flow diagram showing yet another embodiment of a stimulation procedure for disrupting undesired neural activity through desynchronization of action potential propagation along patient tissue. In step 802, first and second electrodes are positioned at first and second stimulation locations, respectively. The first electrode (or first set of electrodes) is a transcutaneous electrode (or set of electrodes) disposed along the patient's skin and the second electrode (or second set of electrodes) is an implanted electrode (or set of electrodes) implanted inside the patient. Positioning the first electrode (or first set of electrodes) at the first stimulation location may, optionally, include removably adhering the electrode(s) to the patient's skin. A computer model may be used to facilitate the determination of the positioning of the first and second electrodes.

Optionally, in step 804, patient pain is detected. The pain may be detected using any suitable technique including, for example, a pain measurement scale, patient feedback, a change in one or more monitored pain indicators (e.g., a frequency shift in the patient's theta wave activity), or the like. The pain indicator, such as a frequency shift, can be detected using any suitable monitoring technique (e.g., electroencephalography, or the like). The monitoring of the pain indicator can be performed using a sensor in communication with the one or more control modules.

In step 806, a first effective electric field is generated using electrical stimulation energy from the first electrode (or first set of electrodes). In step 808, a second effective electric field is generated using electrical stimulation energy from the second electrode, with the second effective electric field being coordinated with the first effective electric field.

The generated second effective electric field may be either overlapping or non-overlapping with the first effective electric field. The second effective electric field can have stimulation parameters that are either the same or different from stimulation parameters of the first effective electric field. A computer model may be used to adjust the stimulation parameters of first and second effective electric fields generated by the first and second electrodes, respectively. The computer model(s) can be used to adjust the location, the size, the shape (or any combination of the above) so that the generated effective electric fields have a desired amount overlap (or do not overlap). Stimulation, via the first and second electrodes, may be initiated in response to the pain indicator, such as the detected frequency shift in the patient's theta band activity. The frequencies of the first and second effective electric fields can be based, at least in part, on the pain indicator, such as the frequency of the detected shift in theta band activity. The stimulation parameters of the first and/or second effective electric fields may be adjusted in response to a feedback loop, such as an observed frequency shift towards or away from a particular frequency or frequency range. The stimulation may be terminated in response to a feedback loop, such as an observed frequency shift towards or away from a particular frequency or frequency range.

It will be understood that the system can include one or more of the methods described hereinabove with respect to FIGS. 6-8 in any combination. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks or described for the control modules, external programming units, remote data storage units, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A transcutaneous electrical stimulation system, comprising:
    a transcutaneous control module comprising a processor, wherein the transcutaneous control module is configured and arranged to provide electrical stimulation signals to a plurality of electrode sets electrically-coupled to the transcutaneous control module and configured and arranged to remain external to a patient for transcutaneous electrical stimulation of patient tissue to treat patient pain;
    a first electrode set electrically-coupled to the transcutaneous control module and configured and arranged for placement along patient skin over a first stimulation location, the first electrode set configured and arranged to communicate with the processor and to generate a first effective electric field suitable for transcutaneous stimulation of patient tissue at the first stimulation location using the electrical stimulation signals provided from the transcutaneous control module;
    a second electrode set electrically-coupled to the transcutaneous control module and configured and arranged for placement along patient skin over a second stimulation location, the second electrode set configured and arranged to communicate with the processor and to generate a second effective electric field suitable for stimulating patient tissue at the second stimulation location using the electrical stimulation signals provided from the transcutaneous control module, wherein the second effective electric field is time-delayed from the first effective electric field such that the second effective electric field is out of phase with the first effective electric field; and
    a sensor in communication with the processor, the sensor configured and arranged for monitoring patient theta band activity and detecting frequency shifts,
    wherein the transcutaneous control module is further configured and arranged to provide the electrical stimulation signals to the first electrode set and the second electrode set in response to a first detected shift in frequency of the theta band activity.

2. The transcutaneous electrical stimulation system of claim 1, wherein the processor is configured and arranged for determining a time delay between the electrical stimulation signals to generate the first effective electric field and the electrical stimulation signals to generate the second effective electric field based on the first detected shift in frequency of the theta band activity.

3. The transcutaneous electrical stimulation system of claim 1, wherein the transcutaneous control module is configured and arranged to adjust at least one of amplitude, frequency, impedance, voltage, or pulse width of the electrical stimulation signals provided to the first electrode set and the second electrode set in response to a second detected shift in frequency of the theta band activity.

4. The transcutaneous electrical stimulation system of claim 1, wherein the transcutaneous control module is configured and arranged to terminate the electrical stimulation signals provided to the first electrode set and the second electrode set in response to a third detected shift in frequency of the theta band activity.

5. The transcutaneous electrical stimulation system of claim 1, further comprising a processing unit in communication with the processor, the processing unit configured and arranged for coordinating with the processor to facilitate positioning of the first electrode set and the second electrode set in a spinal cord of the patient.

6. The transcutaneous electrical stimulation system of claim 1, further comprising a processing unit in communication with the processor, the processing unit configured and arranged for coordinating with the processor to adjust at least one of amplitude, frequency, impedance, voltage, or pulse width of at least one of the first effective electric field or the second effective electric field.

7. The transcutaneous electrical stimulation system of claim 1, further comprising an actuator located external to the patient and in communication with the processor, the actuator configured and arranged for causing the transcutaneous control module to at least one of initiate providing the electrical stimulation signals to the at least one lead or terminate providing the electrical stimulation signals to the at least one lead.

8. The transcutaneous electrical stimulation system of claim 1, further comprising a programming unit in communication with the processor, the programming unit configured and arranged for at least one of adjusting a time-delay between the first effective electric field and the second effective electric field, or select between two or more different electrode sets of the plurality of electrode sets for providing the transcutaneous electrical stimulation of patient tissue.

9. A transcutaneous electrical stimulation system, comprising:
a transcutaneous control module comprising a processor, wherein the transcutaneous control module is configured and arranged to provide electrical stimulation signals to a plurality of electrode sets electrically-coupled to the transcutaneous control module and configured and arranged to remain external to a patient for transcutaneous stimulation of patient tissue to treat patient pain;
a first electrode set of the plurality of electrode sets electrically coupled to the transcutaneous control module and configured and arranged for placement along patient skin, the first electrode set configured and arranged to communicate with the processor and to generate a first effective electric field suitable for transcutaneously stimulating a first set of target neurons within patient tissue using the electrical stimulation signals provided from the transcutaneous control module; and
a second electrode set of the plurality of electrode sets electrically coupled to the transcutaneous control module and configured and arranged for placement along patient skin, the second electrode set configured and arranged to communicate with the processor and to generate a second effective electric field suitable for transcutaneously stimulating a second set of target neurons that is different from the first set of target neurons within patient tissue using the transcutaneous electrical stimulation signals provided from the transcutaneous control module, wherein the second effective electric field has an overlap in volume of at least 50% with the first effective electric field.

10. The transcutaneous electrical stimulation system of claim 9, wherein the second set of target neurons is a subset of the first set of target neurons.

11. The transcutaneous electrical stimulation system of claim 9, wherein the second set of target neurons is mutually exclusive of the first set of target neurons.

12. An electrical stimulation system, comprising:
a transcutaneous control module comprising a first processor, wherein the transcutaneous control module is configured and arranged to provide first electrical stimulation signals to a transcutaneous electrode set electrically-coupled to the transcutaneous control module for transcutaneous stimulation of patient tissue to treat patient pain;
a transcutaneous electrode set electrically-coupled to the transcutaneous control module and configured and arranged for placement along patient skin, the transcutaneous electrode set configured and arranged to communicate with the first processor and to generate a first effective electric field suitable for stimulating patient tissue at a first stimulation location using the first electrical stimulation signals provided from the transcutaneous control module;
an implantable control module configured and arranged for implantation in a body of the patient and comprising a second processor in communication with the first processor, wherein the implantable control module is configured and arranged to provide second electrical stimulation signals to at least one implantable electrode electrically-coupled to the implantable control module for stimulation of patient tissue to treat patient pain; and
at least one implantable electrode electrically-coupled to the implantable control module and configured and arranged to communicate with the second processor and to generate a second effective electric field suitable for stimulating patient tissue at a second stimulation location using the second electrical stimulation signals provided from the implantable control module, wherein the second effective electric field is coordinated with the first effective electric field.

13. The electrical stimulation system of claim 12, wherein the second effective electric field is time-delayed from the first effective electric field such that the second effective electric field is out of phase with the first effective electric field.

14. The electrical stimulation system of claim 12, further comprising a sensor in communication with at least one of the first processor or the second processor, the sensor configured and arranged for monitoring patient theta-band activity and detecting frequency shifts.

15. The electrical stimulation system of claim 12, wherein the second effective electric field has an overlap in volume of no more than 20% with the first effective electric field.

16. The electrical stimulation system of claim 12, wherein the first effective electric field is suitable for stimulating a first set of target neurons within patient tissue using the first electrical stimulation signals, wherein the second effective electric field is suitable for stimulating a second set of target neurons that is different from the first set of target neurons within patient tissue using the second electrical stimulation signals, and wherein the second effective electric field has an overlap in volume of at least 50% with the first effective electric field.

17. The electrical stimulation system of claim 16, wherein the second set of target neurons is a subset of the first set of target neurons.

18. The electrical stimulation system of claim 16, wherein the second set of target neurons is mutually exclusive of the first set of target neurons.

\* \* \* \* \*